United States Patent [19]

Matsuda et al.

[11] Patent Number: 5,128,170
[45] Date of Patent: Jul. 7, 1992

[54] METHOD FOR MANUFACTURING MEDICAL DEVICE HAVING A HIGHLY BIOCOMPATIBLE SURFACE

[75] Inventors: Takehisa Matsuda, Minoo; Kazuhiko Inoue, Kobe; Nobutaka Tani, Osaka, all of Japan

[73] Assignee: Kanegafunchi Kagaku Kogyo Kabushiki Kaisha, Osaka, Japan

[21] Appl. No.: 520,902

[22] Filed: May 9, 1990

[30] Foreign Application Priority Data

| May 11, 1989 | [JP] | Japan | 1-118222 |
| Jun. 1, 1989 | [JP] | Japan | 1-140576 |
| Sep. 25, 1989 | [JP] | Japan | 1-248440 |

[51] Int. Cl.$^5$ .......................... B05D 3/06; A61F 2/00
[52] U.S. Cl. .................................. 427/2; 427/53.1; 427/54.1; 427/44
[58] Field of Search ............... 427/2, 53.1, 54.1, 55, 427/56.1, 35, 36, 44

[56] References Cited

U.S. PATENT DOCUMENTS

| 3,911,164 | 10/1975 | Sayigh et al. | 427/53.1 |
| 3,954,583 | 5/1976 | Lednicer et al. | 204/158 R |
| 3,959,080 | 5/1976 | Orth et al. | 195/63 |
| 3,969,543 | 7/1976 | Roberts et al. | 427/54.1 |
| 4,273,873 | 6/1981 | Sugitachi et al. | 435/181 |
| 4,696,286 | 9/1987 | Cochrum | 435/182 |
| 4,898,951 | 2/1990 | Symons | 435/6 |
| 4,973,493 | 11/1990 | Guire | 427/2 |

FOREIGN PATENT DOCUMENTS

| 0106004 | 4/1984 | European Pat. Off. . |
| 0166998 | 1/1986 | European Pat. Off. . |
| 0214089 | 7/1986 | European Pat. Off. . |
| 2200281 | 4/1974 | France . |

OTHER PUBLICATIONS

Aiba et al. (Nov. 1987) Biomaterials 8:481–488.
Watanabe et al. (1981) Journal of Biomedical Materials Research 15:553–563.

*Primary Examiner*—Marianne Padgett
*Attorney, Agent, or Firm*—Armstrong & Kubovcik

[57] ABSTRACT

A medical device having a highly biocompatible surface wherein hydrophilic polymer is bonded onto a surface of the medical device covalently through a nitrogen atom, and a method for manufacturing a medical device having a highly biocompatible surface comprising the steps of applying a hydrophilic polymer having azido group and/or a composition comprising a compound having at least two azido group and a hydrophilic polymer onto the surface of the medical device, and irradiating the biocompatible material with light so that the hydrophilic polymer is bonded to the medical device surface. The device has sufficient biocompatibility, medical functional capability and economical efficiency. The method easily provides a medical device with sufficient biocompatibility without impairing the device's medical functional capability and economical efficiency.

2 Claims, No Drawings

METHOD FOR MANUFACTURING MEDICAL DEVICE HAVING A HIGHLY BIOCOMPATIBLE SURFACE

BACKGROUND OF THE INVENTION

The present invention relates to a medical device having a highly biocompatible surface and a method for manufacturing the same.

Recently, the advance of medical science has been associated with the development of various medical devices. These medical devices are required to have sufficient medical functional capability, biocompatibility and economical efficiency. The medical functional capability means characteristics controlled by the shape and dynamic feature of a device, for example, a function of storage of blood for a blood bag, a function of dialysis or filtration of blood for a dialyzer of an artificial kidney or for a filtration membrane, a function as a blood pump for an artificial heart and a function as a lens for a contact lens.

The biocompatibility means the nature of a medical device by which the device gives no damage to biocomponents such as biotic tissue and body fluid when the medical device contacts them, namely the nature to secure safety. This is controlled by the surface properties of the medical devices, in particular thin layer from the surface having the roughness of for example 100 Å, which contacts biocomponents such as biotic tissue and body fluid.

Although the medical devices which have been developed have sufficient medical functional capability, they have a drawback that the application procedure in use is limited because of their insufficient biocompatibility. In particular, medical devices to be in contact with blood have an important drawback that thrombus are built up at a region in contact with blood, complements are activated and so on.

Based on such background, there have been positively promoted a research in which a suitable surface modification is performed so that biocompatibility thereof is improved with sufficient medical functional capability being ensured.

For example, there is known a method to improve biocompatibility of the device by means of a process in which radiation exposure or glow discharge treatments is carried out against a device material surface for the purpose of a graft polymerization of hydrophilic monomer such as acrylamide and ethylene glycol, whereby a surface having hydrophilic property is provided. However, this method has many drawbacks, for example, that an apparatus for the treatment is expensive and it lowers economical efficiency, that it is difficult to graft uniformly in case of a device having a hollow inner surface or a complex shape and that it is difficult to graft hydrophilic polymer per se.

As an example of an alternative method taking advantage of bioactive substance, there is developed a method for preventing a thrombus from building up by means of a control release of heparin from a medical device surface or an immobilization of urokinase onto the surface. However, these methods have drawbacks, for example, that thrombus are still built up after sustained release of heparin ceases or after urokinase is devitalized, and furthermore that the shaping method and the base material allow limited selection and concurrently increase the cost.

On the other hand, there are widely applied compounds having photosensitive group such as azido group in the field of photography, typography, adhesion, coating technology and the like. Particularly in the filed of the photoresist, various compounds having azido group are put into practical use. But no attempt has been proposed to apply this technology to biocompatible medical devices.

The present invention was made to solve the problem namely there has not been developed a medical device which has a highly biocompatible surface and at the same time has sufficient medical functional capability and economical efficiency.

An object of the present invention is to provide a medical device having sufficient biocompatibility, medical functional capability and economical efficiency and a method for manufacturing the same.

SUMMARY OF THE INVENTION

After repeated earnest researches relating to a method intended to provide a surface of a medical device with a highly biocompatible surface firmly, stably and economicaly, the present inventors found against the above mentioned problem a solution in which (a) hydrophilic polymer having azido group and/or (b) a composition comprising a chemical compound having at least two azido groups and hydrophilic polymer is applied onto a surface of a medical device and then irradiated for a short time, thereby azido groups are converted into reactive nitrene groups, so that bondings covalently through nitrogen atom are produced between the medical device surface and hydrophilic polymer, and also among hydrophilic polymer molecules, and thus a layer of hydrophilic polymer is bonded onto the medical device. The present invention was made on the basis of this finding. Namely the present invention relates to a medical device having a highly biocompatible surface characterized in that a hydrophilic polymer is bonded onto the surface of the medical device covalently through a nitrogen atom.

The present invention also relates to a method for manufacturing a medical device having a highly biocompatible surface which comprises the steps of applying at least one biocompatible material selected from the group consisting of (a) a hydrophilic polymer having azido group and (b) a composition comprising a compound having at least two azido groups and a hydrophilic polymer onto the surface of the medical device, irradiating with light on to the biocompatible material thereby bonding the hydrophilic polymer to the medical device surface.

Further the present invention relates to a method for manufacturing a medical device having a highly biocompatible surface which comprises the steps of applying a composition comprising a compound having at least two azido groups and a hydrophilic polymer onto the surface of the medical device, and irradiating a light to the composition thereby bonding the hydrophilic polymer to the medical device surface.

DETAILED DESCRIPTION

In the present invention, as described above, bondings covalently through nitrogen atom are produced between a surface of a medical device material and hydrophilic polymer or additionally among hydrophilic polymer molecules, whereby a layer of hydrophilic polymer is bonded onto the material surface. The bondings covalently through nitrogen atom are produced by the reaction of azido group in the compound having azido group.

Examples of the compound having azido group are, for instance, a compound having carbonylazido group (R—CON₃), a compound having sulfonylazido group (R—SO₂N₃) and a compound having aromatic azido group

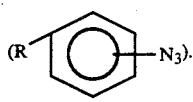

Above all, a compound having aromatic azido group and a compound having sulfonylazido group are preferable because of the good stability. Particularly, a compound having aromatic azido group having electron attractive substituent such as nitro group and a bisazido compound photosensitive against i-line or g-line are more preferable in respect that they can be converted into nitrene by irradiation with a light having a relatively longer wavelength (>320 nm). Examples of a compound having at least two azido groups are, for instance, general bisazido compounds such as those described in Table 1, azido-containing-polymer having at least two azido groups introduced into one molecule and the like. However, the compound is not limited to these examples.

TABLE 1

| Bisazido compound | Photosensible range |
| --- | --- |
| N₃—⌬—CH₂—⌬—N₃ | deep UV |
| N₃—⌬(Cl)—CH₂—⌬(Cl)—N₃ | deep UV |
| N₃—⌬—O—⌬—N₃ | deep UV |
| N₃—⌬—SO₂—⌬—N₃ | deep UV |
| (N₃)⌬—SO₂—⌬(N₃) (meta) | deep UV |
| N₃—⌬—SS—⌬—N₃ | deep UV |
| N₃—⌬—S—⌬—N₃ | deep UV |
| N₃—⌬(OCH₃)—⌬(OCH₃)—N₃ | i-line |
| N₃—⌬—CH=CH—⌬—N₃ | i-line |

TABLE 1-continued

| Bisazido compound | Photosensible range |
|---|---|
| 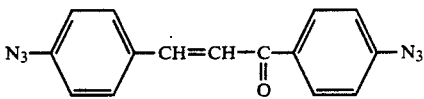 | i-line |
| 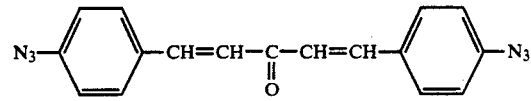 | i-line |
| 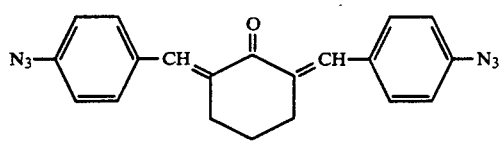 | i-line |
| 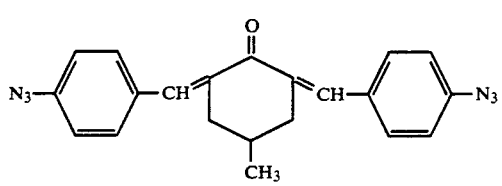 | i-line |
| 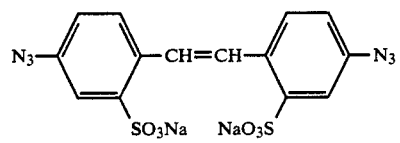 | i-line |
| 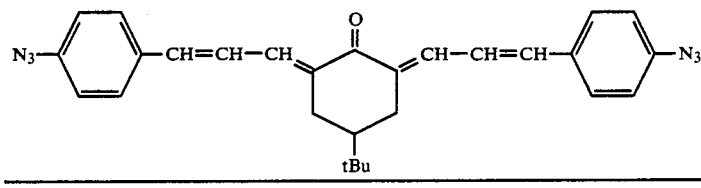 | g-line |

Examples of the hydrophilic polymer are, for instance, a general synthetic hydrophilic polymer, protein, polyose, another polymer having highly biocompatibility. However the hydrophilic polymer is not limited to these examples. With regard to a use of the above-mentioned hydrophilic polymer, any one kind may be used alone or alternatively two or more kinds may be used together.

Examples of the synthetic hydrophilic polymer include, for instance, polyacrylamide, polydimethylacrylamide, polyvinyl alcohol, polyethylene glycol, polyhydroxyethyl methacrylate, polyacrylic acid, polyvinylsulfuric acid, polyallylamine and copolymer of them. However the synthetic hydrophilic polymer is not limited to them. A preferable example is nonionic polymer such as polyethylene glycol in respect that a body fluid component is not easily adsorbed thereto. Especially, more preferable example is arcylamide having no hydroxyl group, such as polyacrylamide and polydimethylacrylamide since complement is less activated.

Examples of the protein include, for instance, albumin, collagen and gelatin and also include enzymes such as urokinase, streptokinase and plasminogen activator. However, the protein is not limited to them. Especially, collagen is preferable in respect of its sufficient tissue compatibility.

Examples of the polyose are, for instance, heparin, hyaluronic acid, chondroitin sulfate, dermatan sulfate, dextran sulfate, keratan sulfate, and heparan sulfate. Especially, heparin is preferable due to its highly anticoagulant activity.

Examples of the above-mentioned another polymer having high biocompability are, for instance, chitin, prostaglandin, a derivative thereof and so on.

The hydrophilic polymer is bonded onto a surface of a medical device covalently through a nitrogen atom. The bonding is produced in a process in which nitrene groups, created through an optical irradiation against azido group, are subjected to chemical reactions shown by reaction formulas given below, namely, a hydrogen-abstruction reaction represented by the formula (1), an insertion into C—H bond or an addition to double bond represented by the formula (2) and coupling reaction represented by the formula (3).

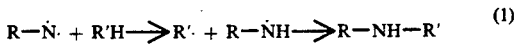

$$R-\dot{N}\cdot + R'H \longrightarrow R'\cdot + R-\dot{N}H \longrightarrow R-NH-R' \quad (1)$$

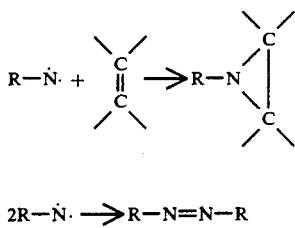

$$2R-\ddot{N}\cdot \longrightarrow R-N=N-R \quad (3)$$

While a nitrene group is so highly reactive that a few bonds can be produced through other reactions than those above-mentioned, it is intended that the present invention should include any devices wherein hydrophilic polymer is bonded onto the medical device surface substantially by virtue of the described bonding.

Furthermore, although the above-mentioned reaction can happen between hydrophilic polymer molecules to cause crosslinking, other similar devices are also included in the scope of the present invention. In case that the hydrophilic polymer is highly water-soluble, crosslinking can be positively enhanced according to circumstances.

In the present invention, a medical device means a device which is in use brought into contact with biocomponents such as biological tissue and body fluid. Examples of the medical device are, for instance, a blood bag, a urinary collecting bag, a blood transfusion set, a suture, a drainage tube, various kinds of catheters, a blood access, a blood circuit, an artificial vessel, an artificial kidney, an artificial lung, a prosthetic heart valve, a plasma exchange membrane, various kinds of adsorbents, CAPD, IABP, a pacemaker, an artificial joint, an artificial caput, dental material, an intraocular lens, soft contact lens and various kinds of shunts, however, the device is not limited to those examples.

Examples of the medical device material are, for instance, synthetic resin and synthetic rubber.

In the medical device, its entire surface may have hydrophilic polymer or only the part to be in contact with biocomponents such as biotic tissue and body fluid may have hydrophilic polymer.

Next, a manufacturing method of a medical device of the present invention is described below.

With regard to hydrophilic polymer having azido group used in the present invention, the number of azido group is one or more. However, in respect to the bonding strength to a surface of a medical device and the stability of a layer of hydrophilic polymer due to crosslinking among hydrophilic polymer molecules, it is preferable that the number of azido group is at least two.

Hydrophilic polymer having azido group can be prepared in the manner, in which, azido group is introduced into hydrophilic polymer by reacting a functional group of hydrophilic polymer with another functional group of a compounds having azido group.

For example, there can be employed a method in which an azido compound having amino group is condensed with hydrophilic polymer having carboxyl group in the presence of condensing agent, a method in which an azido compound having acid chloride group or aldehyde group is reacted with hydrophilic polymer having hydroxyl group, a method in which an azido compound having carboxyl group is condensed with hydrophilic polymer having amino group in the presence of condensing agent, a method in which an azido group having N-hydroxysuccinimide ester group or epoxy group is reacted with hydrophilic polymer having amino group, and so on.

Azido group can be introduced also into polyacrylamide or the like having no other active functional group than amido group. In that case amido group is converted into amino group by means of the known method (Hofmann degradation) and then azido group is introduced taking advantage of this amino group.

As a method of applying hydrophilic polymer with azido group having introduced thereinto onto the device material surface, there can be employed, for example, a method in which aqueous solution or colloidal solution of hydrophilic polymer with azido group having introduced is brought into contact with the device material surface to be adsorbed on the device material surface, a method in which hydrophilic polymer with azido group having introduced is in a liquid form spread or sprayed on the device material surface after being dissolved or suspended in volatile organic solvent such as methanol or the like and subsequently the applied liquid is dried to form a thin layer of hydrophilic polymer on the device material surface or suchlike methods. However, the method is not limited to these examples.

As a method for applying a composition comprising a compound having azido groups and hydrophilic polymer onto the device material surface, there can be employed, for example, a method in which the composition in a liquid form spread or sprayed on the material surface after being dissolved or suspended in volatile organic solvent such as methanol or the like and subsequently the applied liquid is dried to form a thin layer of the composition onto the device material surface, a method in which aqueous solution or colloidal solution of the composition is brought into contact with the device material surface to be adsorbed on the device material surface or similar methods. Furthermore, there also can be employed, for example, a method in which a compound having azido group is applied onto the device material surface, and thereafter hydrophilic polymer is applied thereon.

With respect to the bonding of the applied hydrophilic polymer to the device material surface, the bonding can be achieved easily, by means of, for example, an optical irradiation against hydrophilic polymer having azido group having been applied to the device material surface.

As the hydrophilic material to be applied on the device material surface, a composition comprising a compound having at least two azido groups and the hydrophilic polymer is preferably used in respect that no special operation to introduce azido group into hydrophilic polymer is required and that removal by washing of a component which was not bonded is easy.

As a light source for the irradiation operation, there can be used generally a light source capable of generating ultraviolet rays, for example, various kinds of mercury light such as a high pressure mercury lamp, a low pressure mercury lamp, an extra-high pressure mercury lamp; excimer laser; and the like.

However, in case that there is used on i-line or g-line photosensitive bisazido compound or a compound having aromatic azido group having nitro group or the like which can produce a nitrene group through an irradiation of a light having a wave length not shorter than 320 nm, the influence of a short wave-length ultraviolet rays on hydrophilic polymer of the device material can be reduced by cutting off the short wave-length range using a filter. This method is particularly preferable in case that protein and so on, is used as hydrophilic polymer.

The conversion into nitrene group finishes in a very short time, so five minutes or less duration time is enough for the irradiation of ultraviolet rays.

With respect to a method of irradiation, there can be employed for example a direct irradiation to the device material surface to which hydrophilic polymer have been applied, and alternatively there can be employed in the case of a material capable of transmitting ultraviolet rays an irradiation toward the reveres side surface relative to the surface with applied hydrophilic polymer.

In addition, taking advantage of an optical fiber, it is possible to irradiate any part of an inner surface of a device having a complicated shape.

Although the present invention will be explained below with reference to several Examples, wherein all parts are by weight unless otherwise noted, the present invention is not limited to those specific Examples.

EXAMPLE 1

One part of acrylamide and 4 parts of N,N-dimethylacrylamide were copolymerized in acetone in the presence of a redox catalyst system of benzoyl peroxide and N,N-dimethyl-P-toluidine.

White precipitation product was subjected to separation by filteration and to sufficient washing with acetone, and thus N,N-dimethylacrylamide-acrylamide copolymer (hereinafter represented by PDMA) was obtained.

The PDMA obtained in this manner was subjected to Hofmann degradation in accordance with a well known method so that amido group was converted into amino group (Refer to e.g. Hiroo Tanaka et al, "Hofmann degradation of polyacrylamide", Japanese Journal of Polymer Science and Technology, Vol. 33, No. 6, page 309, (1976)). The reaction mixture was poured into a large amount of acetone, and then polymer was collected. The polymer was dried and then dissolved in a small amount of water so as to be made acidic with hydrochloric acid, and thereafter PDMA with amino group having been introduced (hereinafter represented by amino-containing-PDMA) was obtained by means of reprecipitation from acetone.

100 mg of the amino-containing-PDMA obtained in this manner was dissolved in 10 ml of water, then triethylamine was added thereto to liberate amino group. Thereafter, 100 mg of later described water-soluble azido compound Sulfo-SANPAH (abbreviation, available from PIERCE) was dissolved therein, and this obtained mixture was left overnight being shielded from light. After the removal of low molecular weight impurity by means of dialysis with a dialysis membrane having cutting off molecular weight of 1000, the reaction mixture was freeze-dried and PDMA with azido group having been introduced (hereinafter represented as azido-containing-PDMA1) was obtained.

After the preparation of the methanol solution of the obtained azido-containing-PDMA1 (about 1% by weight), about 25 μl of this solution was applied and spreaded onto a piece of sample film having a cut-off size of about 2 cm². Thereon the solvent was removed through air-drying. Irradiation of ultraviolet rays for one minute against the film surface having a resultant cast of azido-containing APDMA1 was conducted by means of high pressure mercury lamp. After that, the film was washed enough with methanol and water. In this Example, sample films made respectively from polyethylene terephtalate, polystyrene and polyurethane, were used.

It was observed that a film surface having a layer of hydrophilic polymer having formed due to the irradiation from azido-containing-PDMA1 had been notably improved in respect of water-wettability. The result of surface analysis by ESCA proved that a nearly uniform layer of hydrophilic polymer had been formed onto the surface with the thickness of the layer being more than 100 Å.

Both the sample film having the hydrophilic polymer layer obtained in this manner and a original film without having the hydrophilic polymer layer were immersed into platelet-rich plasma prepared from whole blood of normal person and were incubated at 37° C. for an hour, and subsequently they were rinsed with physiological saline solution and were bonded with glutaric aldehyde. Through a observation of the degree of platelet adhesion on these films, it was proved that almost no platelets adhered to the sample film having the hydrophilic polymer layer, while many platelets adhered on the original film having no layer of hydrophilic polymer.

EXAMPLE 2

PDMA with azido group having been introduced (hereinafter represented by azido-containing-PDMA2) was obtained in the same manner as Example 1 except that 100 mg of amino-containing-PDMA and 80 mg of later-described azido compound ANB-NOS (abbreviation, available from PIERCE) were used, and that methanol, instead of water, was used as solvent.

After the solvent was removed, dried azido-containing-PDMA2 was dissolved in a small amount of water. The mixture was dialyzed in the same manner as Example 1 so that azido-containing-PDMA2 was purified, and then a film having a layer of hydrophilic polymer prepared from azido-containing-PDMA2 was obtained in the same manner as Example 1. It was observed that the surface of the film had been notably improved in respect to water-wettability and that almost no adhesion of platelets had taken place. Furthermore, as a result of the surface analysis by ESCA, it was confirmed that the layer of hydrophilic polymer had been formed, equally with Example 1, onto the surface with the thickness of the layer being more than 100 Å.

EXAMPLE 3

PDMA with azido group having been introduced (hereinafter represented by azido-containing-PDMA3) was obtained in the same manner as Example 2 except that 100 mg of amino-containing-PDMA and 65 mg of later-described azido compound HSAB (abbreviation, obtained by dehydration condensation of p-azidobenzoic acid and N-hydroxysuccinimide, in dioxane, in the presence of N,N'-dicyclohexylcarbodiimide). Wherein, HSAB was added after being dissolved in a small amount of tetrahydrofuran (THF).

Thereafter, in the same manner as Example 2, the purification of azido-containing-PDMA3 was carried out, and then a film having a layer of hydrophilic polymer prepared from azido-containing-PDMA3 was obtained in the same manner as Example 1. It was observed that the surface of the film had been notably improved with respect to water-wettability and that almost no adhesion of platelets had taken place. Furthermore as a result of the surface analysis by ESCA, it was confimed that the layer of hydrophilic polymer had been formed, equally with Example 1, onto the surface with the thickness of the layer being more than 100 Å.

EXAMPLE 4

Polyacrylamide having average molecular weight of about 40,000 was subjected to Holfmann degradation in the same manner as Example 1, thereby some of amido groups were converted into amino groups. Reaction mixture was poured into a large amount of methanol and polymer was collected. The polymer after drying was dissolved in a small amount of water so as to be made acid with hydrochloric acid, and then polyacrylamide with amino group having been introduced (hereinafter represented by amino-containing-PAAm) was obtained by means of reprecipitation from methanol. In the same manner as Example 1, polyacrylamide with azido group having been introduced (hereinafter represented by azido-containing-PAAm) was obtained from amino-containing-PAAm and Sulfo-SANPAH.

Aqueous solution of azido-containing-PAAm obtained in this manner (1% by weight) was prepared and a sample film was immersed into the prepared solution and left for an hour. The immersed sample film was irradiated for 5 minutes with ultraviolet rays from high pressure mercury lamp through the solution. Then the sample film was taken out and washed with water sufficiently. In this Example Teflon film and polystyrene film were used as sample films. It was observed that a film having a layer of hydrophilic polymer having formed from azido-containing-PAAm had been notably improved in respect of water-wettability and that almost no platelet adhesion had taken place. Furthermore, the result of surface analysis by ESCA proved that a layer of the hydrophilic polymer had been formed onto the film surface with thickness of the layer being more than 100 Å.

EXAMPLE 5

1 g of bovine serum albumine was dissolved into 0.15 mol of phosphoric acid buffer (pH 8.5) so as to prepare about 10% by weight solution. 10 mg of the water-soluble azido compound Sulfo-SANPAH was added and dissolved into this solution, and thereafter this mixture was left, in a refrigerator, being shielded from light so that azido group was introduced into albumin.

In this mixture, polystyrene film having a cut-off size of about 2 cm$^2$ was immersed for an hour, thereby albumin with azido group having been introduced was adsorbed onto the film surface. The film was taken out and rinsed by physiological saline solution. After that, irradiation against the film with ultraviolet rays using high pressure mercury lamp was conducted for five minutes, wherein the range having wave-length of not longer than 310 nm was cut-off by an ultraviolet filter. Then the film was washed sufficiently with physiological saline solution.

It was observed that the surface of the film having a layer of albumin obtained in this manner had been notably improved with respect to water-wettability and that almost no adhesion of platelets had taken place. Furthermore as a result of the surface analysis by ESCA, it was confirmed that the layer of albumin had been formed onto the surface with the thickness of the layer being more than 100 Å.

EXAMPLE 6

10 parts of PDMA obtained in Example 1 and one part of 2,6-di-(4'-azidobenzylidene) cyclohexanone as bisazide compound were mixed and dissolved in methanol so as to prepare about 1% by weight solution. In this Example, a film of polyethylene terephtalate was used. Then, in the same manner as Example 1, a film having a layer of hydrophilic polymer was obtained, and the obtained film was tested. It was observed that the surface of the film had been notably improved with respect to water-wettability and that almost no adhesion of platelets had taken place. Furthermore, as a result of the surface analysis by ESCA, it was confirmed that the layer of hydrophilic polymer resulted from PDMA had been formed onto the surface with the thickness of the layer being more than 100 Å.

EXAMPLE 7

N,N-dimethylacrylamide monomer (available from Kohjin Co., Ltd) was copolymerized in acetone in the presence of a redox catalyst system of benzoyl peroxide and N,N-dimethyl-P-toluidine so that poly(N,N-dimethylacrylamide) (hereinafter represented by PDMAA) was obtained.

95 parts of PDMAA obtained in this manner and 5 parts of 2,6-di-(4'-azidobenzylidene)-cyclohexanone as bisazide compound were mixed and dissolved in methanol so as to prepare about 1% by weight solution.

About 20 μl of this solution was applied and spreaded onto a piece of sample film having a cut-off size of about 2 cm$^2$. Then the solvent was removed through air-drying. Irradiation of ultraviolet rays for one minute against the film surface having a resultant cast of PDMAA containing bisazide compound was conducted by means of high pressure mercury lamp. After that, the film was washed enough with methanol and water. In this Example, there were used sample films made respectively from polyethylene terephtalate, polystyrene and polyurethane.

It was observed that a film surface having a layer of hydrophilic polymer having formed due to the irradiation from azido-containing-PDMA1 had been notably improved in respect of water-wettability and that almost no adhesion of platelets had taken place. The result of surface analysis by ESCA proved that a nearly uniform layer of hydrophilic polymer had been formed onto the surface with the thickness of the layer being more than 100 Å.

EXAMPLE 8

1 g of bovine serum albumin was dissolved into 0.15 mol of phosphoric acid buffer (pH8.5) so as to prepare about 10% by weight solution. 10 mg of the water-soluble bisazido compound of sodium 4,4'-diazidostilbene-2,2'-disulfonate was added and dissolved into this solution.

In this mixture, polystyrene film having a cut-off size of about 2 cm$^2$ was immersed for an hour, thereby albumin comprising water-soluble bisazido compound was adsorbed onto the film surface. The film was taken out and rinsed by physiological saline solution. After that, irradiation against the film with ultraviolet rays using high pressure mercury lamp was conducted for five minutes, wherein the range having wave-length of not longer than 310 nm was cut-off by an ultraviolet filter. Then the film was washed sufficiently by physiological saline solution.

It was observed that the surface of the film having a layer of albumine obtained in this manner had been notably improved with respect to water-wettability and that almost no adhesion of platelets had taken place. Furthermore, as a result of the surface analysis by ESCA, it was confirmed that the layer of albumin had been formed onto the surface with the thickness of the layer being more than 100 Å.

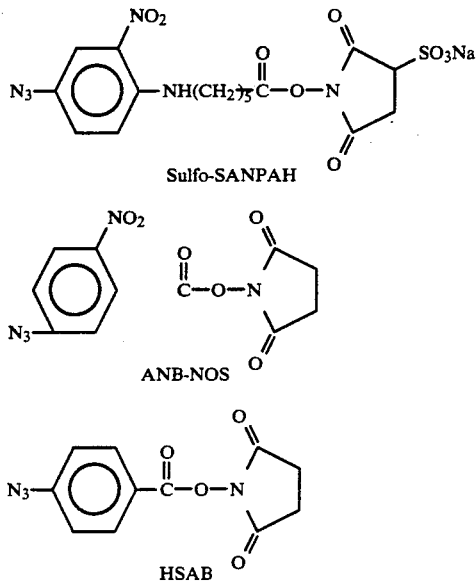

The medical device of the present invention having a surface comprising highly biocompatible hydrophilic polymer exhibits sufficient biocompatibility when it is brought into contact with biocomponents such as biotic tissue and body fluid, and therefore the medical device of the present invention ensures high degree of safety.

In accordance with the medical device manufacturing method of the present invention, a hydrophilic polymer can be easily bonded onto the device material surface by conducting a process in which a hydrophilic polymer having azido group and/or a composition comprising a compound having at least two azido groups and a hydrophilic polymer is appied onto a surface of a medical device and then irradiated. Accordingly, the method of the present invention enables various kinds of materials to be used for medical devices because not only a conventional device material but also a less biocompatible material which has been unsuitable to a medical device can be easily provided with a highly biocompatible surface. Furthermore, the method of the present invention brings another advantage that the medical functional capability and the economical efficiency of the medical device are not impaired because only thin layer from the surface of the medical device is modified.

What is claimed is:

1. A method for manufacturing a medical device having a highly biocompatible surface which comprises the steps of applying a composition comprising a compound having at least two azido groups and a hydrophilic polymer onto the surface of the medical device, and irradiating the applied composition with light to convert the azido groups to nitrene groups thereby bonding the hydrophilic polymer to the surface of the medical device and crosslinking the hydrophilic polymer.

2. A method for manufacturing a medical device having a biocompatible surface which comprises applying a least one biocompatible material onto the surface of the medical device, said at least one biocompatible material being selected from the group consisting of a hydrophilic polymer having at least two azido groups and a composition comprising a compound having at least two azido groups and a hydrophilic polymer; and irradiating the applied biocompatible material with light to convert the azido groups into nitrene groups, thereby bonding the hydrophilic polymer covalently to the surface of the medical device and crosslinking the hydrophilic polymer.

* * * * *

UNITED STATES PATENT AND TRADEMARK OFFICE
CERTIFICATE OF CORRECTION

PATENT NO. : 5,128,170
DATED : July 7, 1992
INVENTOR(S) : Matsuda, et. al.

It is certified that error appears in the above-indentified patent and that said Letters Patent is hereby corrected as shown below:

Title page, item [73], Assignee:  first line, "Kanegafunchi" should read -- Kanegafuchi--.

In Column 9, Line 30, "-P-toluidine" should read "
should read -- -p-toluidine--.

In Column 13, Line 20, a bond is missing

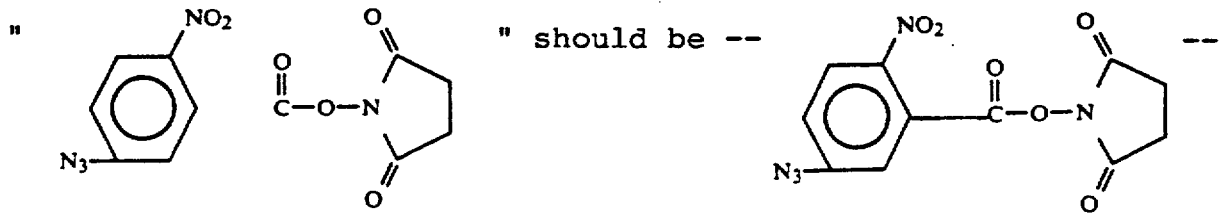

In Column 14, Line 30, "a least" should read as --at least--.

Signed and Sealed this

Twentieth Day of September, 1994

Attest:

BRUCE LEHMAN

*Attesting Officer*     *Commissioner of Patents and Trademarks*